United States Patent
Yun et al.

(10) Patent No.: US 8,062,596 B2
(45) Date of Patent: Nov. 22, 2011

(54) APPARATUS FOR DETECTING NANO PARTICLE HAVING NANO-GAP ELECTRODE

(75) Inventors: Wan Soo Yun, Daejeon (KR); Hyung Ju Park, Busan (KR); Cho Yeon Lee, Icheon-si (KR)

(73) Assignee: Korea Research Institute of Standards and Science, Daejeon (KR)

( * ) Notice: Subject to any disclaimer, the term of this patent is extended or adjusted under 35 U.S.C. 154(b) by 0 days.

(21) Appl. No.: 12/810,461

(22) PCT Filed: Nov. 10, 2008

(86) PCT No.: PCT/KR2008/006616
§ 371 (c)(1),
(2), (4) Date: Jun. 24, 2010

(87) PCT Pub. No.: WO2009/084810
PCT Pub. Date: Jul. 9, 2009

(65) Prior Publication Data
US 2010/0282605 A1    Nov. 11, 2010

(30) Foreign Application Priority Data

Dec. 31, 2007   (KR) .................. 10-2007-0141326

(51) Int. Cl.
G01N 7/00    (2006.01)
G01N 21/00   (2006.01)
(52) U.S. Cl. ....... 422/83; 422/98; 422/82.01; 422/82.02
(58) Field of Classification Search .................... 422/98, 422/83, 82.01, 82.02
See application file for complete search history.

(56) References Cited

U.S. PATENT DOCUMENTS

| | | | |
|---|---|---|---|
| 5,506,673 A | | 4/1996 | Kosaka et al. |
| 6,737,286 B2 | * | 5/2004 | Tao et al. ................. 438/17 |
| 6,824,974 B2 | | 11/2004 | Pisharody et al. |
| 6,849,911 B2 | * | 2/2005 | Monty et al. .............. 257/414 |
| 6,878,539 B1 | * | 4/2005 | Fritzsche et al. ........ 435/287.2 |
| 7,030,452 B2 | * | 4/2006 | Tao et al. ................. 257/414 |
| 7,104,111 B2 | * | 9/2006 | Monty et al. .............. 73/23.2 |
| 7,237,429 B2 | * | 7/2007 | Monty et al. .............. 73/23.2 |
| 7,367,215 B2 | * | 5/2008 | Monty et al. .............. 73/23.2 |
| 7,385,295 B2 | * | 6/2008 | Son et al. ................. 257/776 |
| 7,537,883 B2 | * | 5/2009 | Yu et al. .................. 430/313 |

(Continued)

FOREIGN PATENT DOCUMENTS

KR    100294678 B1    7/2001

(Continued)

Primary Examiner — Brian J Sines
(74) Attorney, Agent, or Firm — The Webb Law Firm

(57) ABSTRACT

The present invention relates to a nanoparticle sensor which is capable to identify an existence/nonexistence, a concentration, a size distribution and a component of the nanoparticles using an electrode pair having a separated distance of a nano-gap, in which the nanoparticle sensor includes a unit element configured with a plurality of unit electrodes electrically operated independently from each other and detects the nanoparticles based on the number of the unit electrodes electrically changed due to the nanoparticles captured into the nano-gap. The nanoparticle sensor of the present invention can detect the component, the size, the size distribution and the concentration of the nanoparticles by single measurement, have high reliability and regeneration while reducing a detection time by statistical method via a plurality of electrode pairs having the nano-gap, and detect even very low concentration of nanoparticles.

13 Claims, 5 Drawing Sheets

U.S. PATENT DOCUMENTS

| | | |
|---|---|---|
| 2003/0087277 A1* | 5/2003 | Fritzsche et al. ............ 435/6 |
| 2004/0067646 A1* | 4/2004 | Tao et al. .................. 438/689 |
| 2005/0201660 A1 | 9/2005 | Grot et al. |
| 2005/0285275 A1* | 12/2005 | Son et al. ................. 257/773 |
| 2008/0218753 A1 | 9/2008 | Chang et al. |
| 2009/0084686 A1 | 4/2009 | Yun et al. |
| 2010/0098966 A1 | 4/2010 | Ah et al. |
| 2010/0184062 A1* | 7/2010 | Steinmuller-Nethl et al. ... 435/6 |

FOREIGN PATENT DOCUMENTS

| | | |
|---|---|---|
| KR | 100315992 B1 | 6/2002 |
| KR | 100670590 B1 | 1/2007 |
| KR | 100762258 B1 | 10/2007 |
| KR | 100777973 B1 | 11/2007 |

* cited by examiner

【Figure 1】
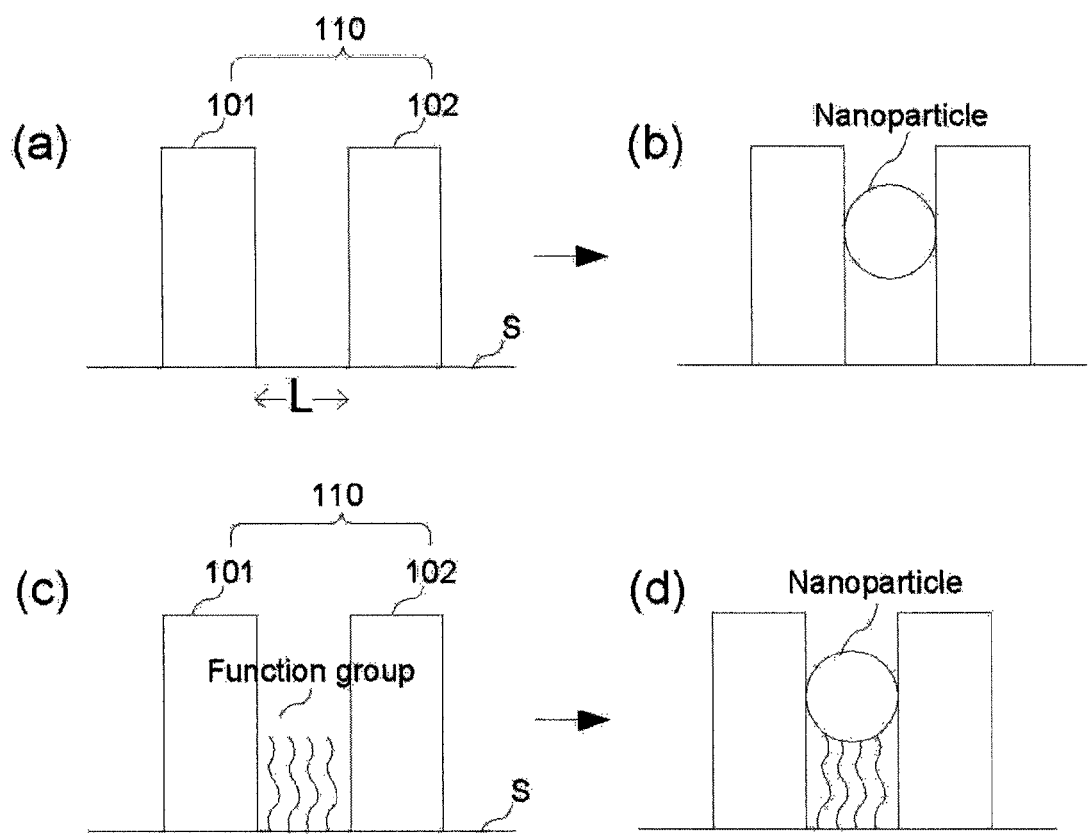

[Figure 2]
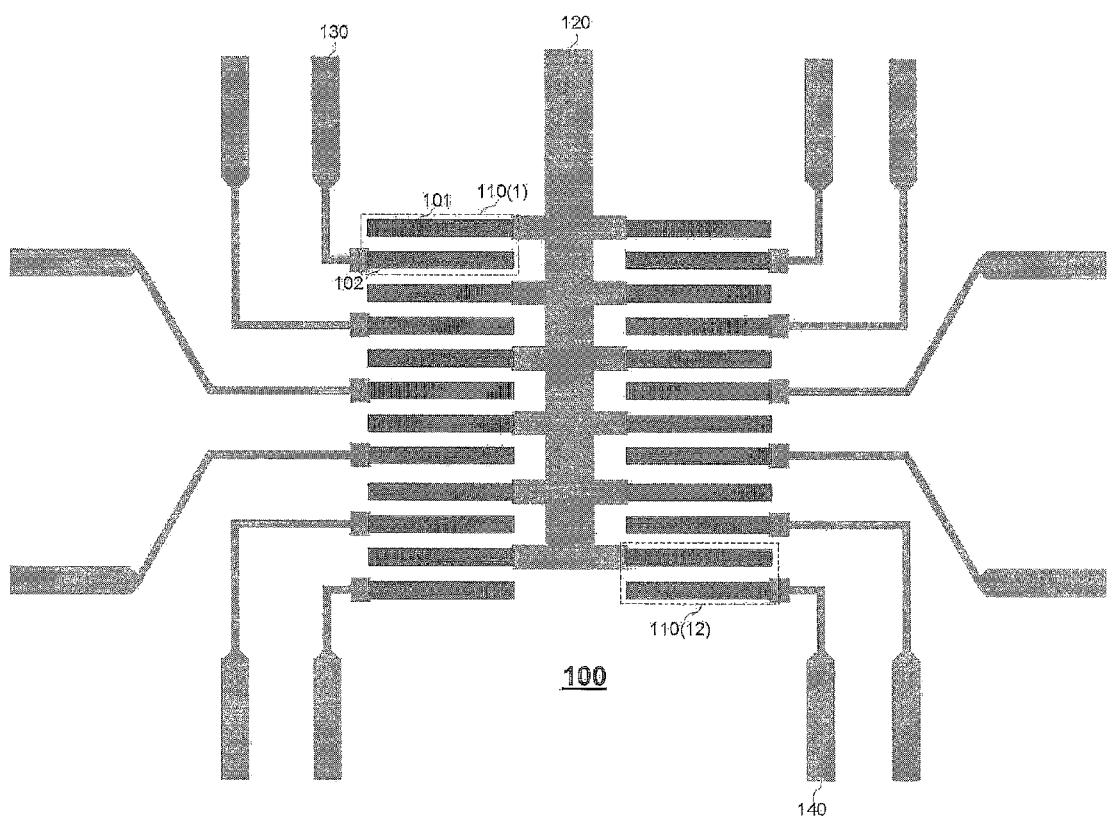
100

[Figure 3]
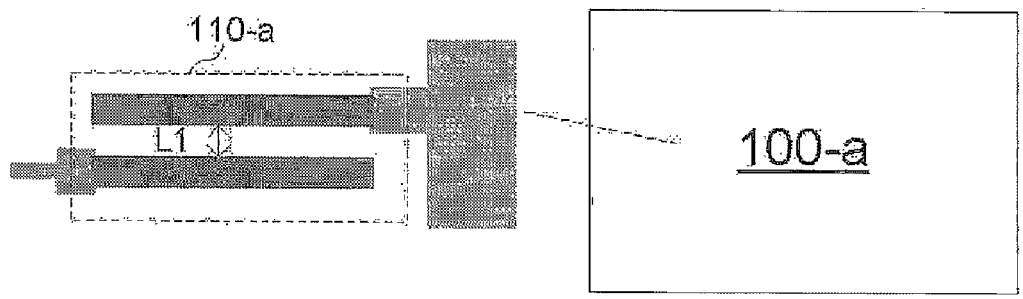
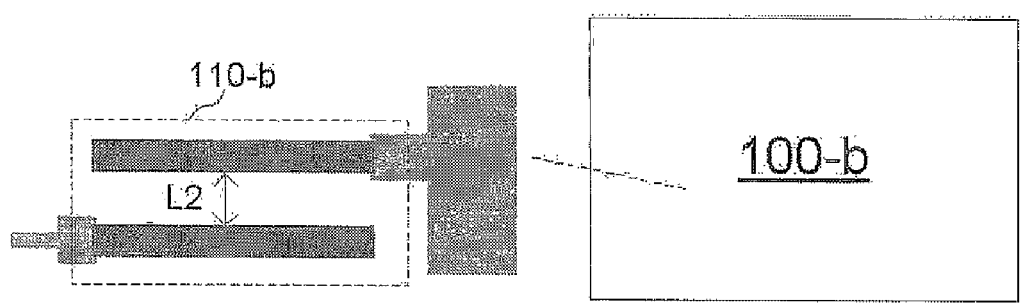
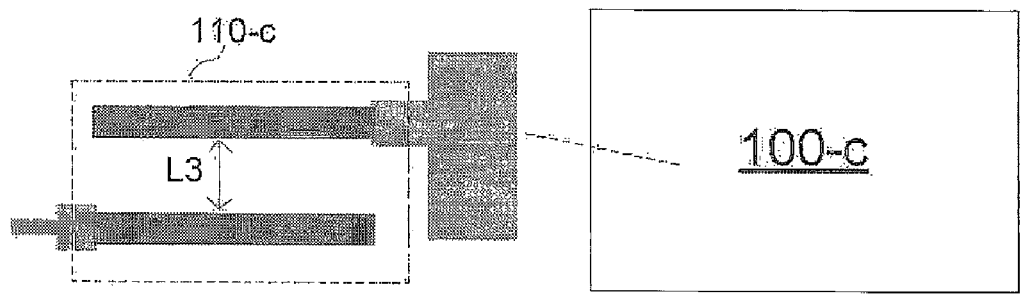

【Figure 4】
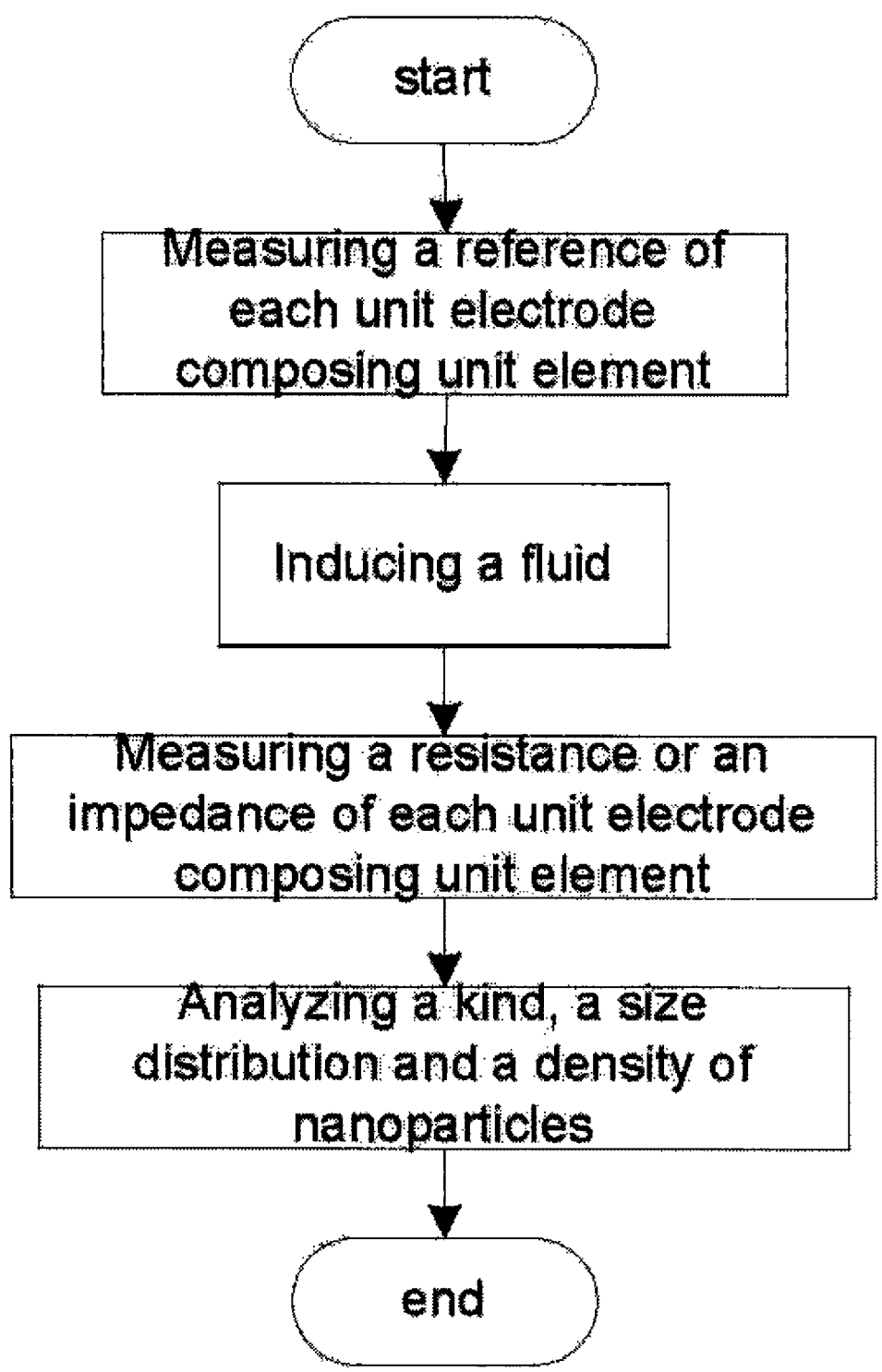

[Figure 5]
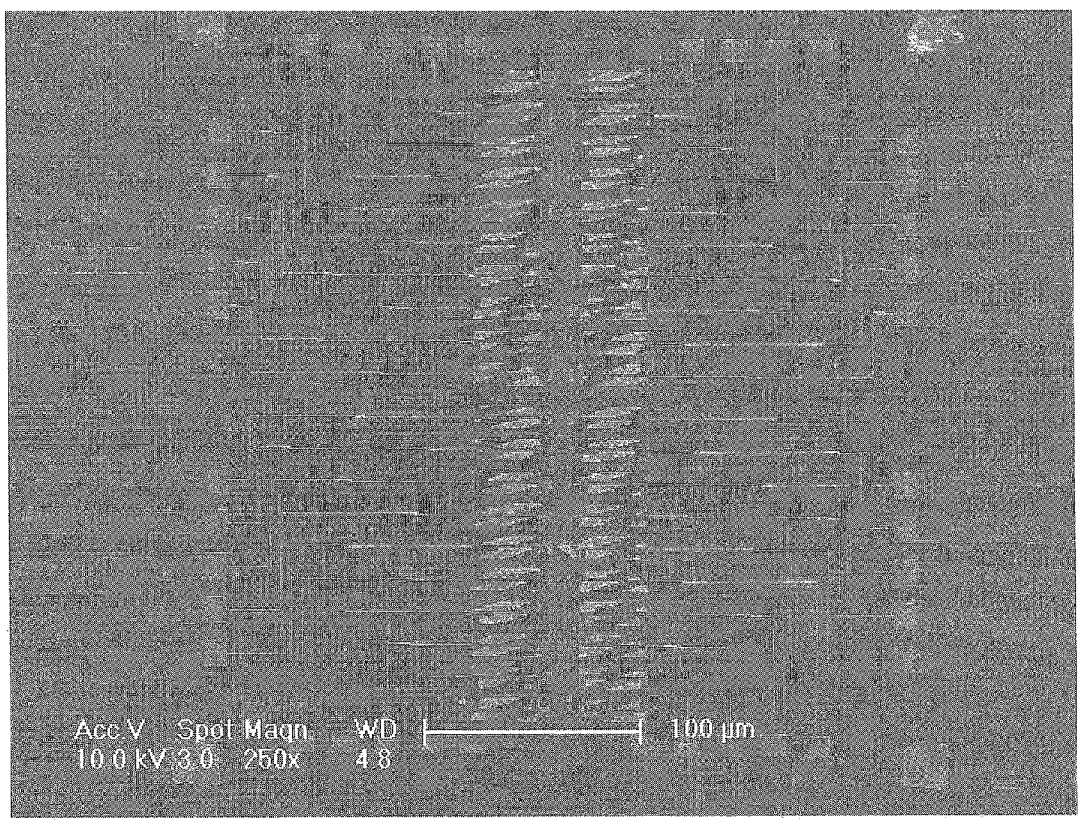

APPARATUS FOR DETECTING NANO PARTICLE HAVING NANO-GAP ELECTRODE

TECHNICAL FIELD

The present invention relates to a system and method for detecting nanoparticles through an electrical device which is capable to identify an existence/nonexistence, a concentration, a size distribution and a component of the nanoparticles using an electrode pair having a separated distance of a nano-gap.

BACKGROUND ART

As technologies for synthesis and size control of the nano-particles are advanced, it has been widely used. Thus new product based on nanotechnology has already appeared on the market and also have been developed. However, the large-scale discharge of engineered nanoparticles into the environment can potentially threaten the human and environmental health, safety problems of the nanoparticles become a pending problem.

Therefore, a demand for technology to identify the existence/nonexistence and a nanoparticle concentration should be increased to solve them. This is becoming important concerns to research an influence which the nanoparticles can exert on the surrounding and environment.

The existing particle sensor (Korean Patent Registration No. 10-0315992) is a device of detecting micro scale particle or corpuscles in the air other instead of detecting nano scale particle in all around condition, which does not have a sufficient sensitivity and accuracy to identify the existence/nonexistence and the quantity of the particular nanoparticles.

Also, recently presented nanoparticles sensor (Korean Patent Registration No. 10-0670590 and U.S. Patent Laid-Open No. 2005-0201660) is using an optical method or an electrochemical method as a method of detecting the particles.

However, there is a need for developing the particle sensor using a chip-type electronic element in order to manufacture a sensor for use in detection which can be measured rapidly with a low cost while being portable and convenient to be used.

Further, the chip-type particle sensor which is made smaller via a typical semiconductor process can be applied to various fields in a such way that it is directly bonded to the electronic machine, handheld machine, or consumer electronics which are widely used, and make it easier to detect the nanoparticles in a direct manner other than in the air and within a fluid and thus make possible ordinary monitoring within various media, which are not possible in the existing technologies.

DISCLOSURE

Technical Problem

An object of the present invention is to provide a nanoparticle sensor using a chip-type electronic element which is capable to identify a component, an existence/nonexistence, a concentration and a size distribution of the nanoparticles with high reliability and regeneration by single measurement.

Technical Solution

To achieve the above objects, a nanoparticle sensor for detecting nanoparticles according to the present invention is characterized in that one pair of electrodes separated at a distance to have a nano-gap is provided as a unit electrode, and the nanoparticles are detected by measuring an electric change caused due to the nanoparticles captured into the nano-gap.

Preferably, the nanoparticle sensor comprises a unit element configured with a plurality of the unit electrodes which is electrically operated independently from each other, and the nanoparticle are characterized by the number of the unit electrodes which is electrically changed due to the nanoparticles captured into the nano-gaps.

In other words, the nanoparticle sensor of the present invention can be configured with unit electrodes to detect an existence/nonexistence of the nanoparticles, can be configured with the unit element composed with a plurality of unit electrodes to detect a kind, a concentration, a size and a size distribution of the nanoparticles by measuring the number of the unit electrodes electrically changed due to the nanoparticles captured into the nano-gap.

The detection size limit of nanoparticles was characterized by controlling a size of the nano-gap.

At this time, the unit element is configured with the unit electrodes having various nano-gap sizes to identify the size distribution of the nanoparticles, and the unit electrodes have a plurality of the same nano-gap size to identify the nanoparticle concentration.

For the purpose of reliability and accuracy, the nanoparticle sensor is preferably configured with a plurality of unit elements having various nanogap sizes, and a size distribution of the nanoparticles is preferably characterized by the number of the unit electrodes of which a resistance or an impedance is changed of the same unit element for each of the plurality of unit elements.

In order to measure a change in the resistance or the impedance, the resistance or the impedance of each unit electrode measured ab-initio without induction of the nanoparticles is referred to as a reference value, and a fluid containing the nanoparticles is induced into the nanoparticle sensor and then the resistance or the impedance of each unit electrode is re-measured after passing a certain time. At this time, the fluid can be a liquid or a gas into which the nanoparticles are dispersed.

As described above, the size, the size distribution and the existence/nonexistence of the nanoparticles can be characterized by controlling the size of the nano-gap formed in the unit electrodes.

Preferably, a function group combining with a particular nanoparticle is formed on a surface of the nano-gap, in order to discriminate a component of the nanoparticles.

At this time, the unit element is configured with a plurality of unit electrodes having the nano-gaps in which the different function group is formed.

At this time, the unit element is configured with a plurality of unit electrodes having the nano-gaps in which the same function group is formed, and the nanoparticle sensor is configured with a plurality of unit elements in which the function group different from one another is formed.

The electrical change takes a change in a resistance or an impedance of the unit electrode, in order to identify the existence/nonexistence, the component, the size distribution, and the size of the nanoparticles.

Preferably, the nanoparticle concentration is characterized by dividing a total number of the unit electrodes of which a resistance or an impedance is changed into a total number of the unit electrodes composing the unit element.

The nanoparticle sensor can be configured with at least one unit element, in which one electrode which is selected respectively from all the unit electrodes composing the unit element is connected to a single metal line. Further, the other electrodes which are not connected to the single metal line of the unit electrodes are connected to an independent metal line for applying a voltage, respectively.

Advantageous Effects

According to the nanoparticle sensor of the present invention, there are advantage in that it can identify the component, the size, the size distribution and the concentration of the nanoparticles by single measurement, it has high reliability and regeneration while reducing a detection time by statistical method via a plurality of electrode pairs having the nano-gap, and it can identify even very low concentration of nanoparticles. As well, according to the nanoparticle sensor of the present invention, there are some advantages: higher integration, small size and low manufacturing cost, since it can be produced using a typical semiconductor process.

DESCRIPTION OF DRAWINGS

The above and other objects, features and advantages of the present invention will become apparent from the following description of preferred embodiments given in conjunction with the accompanying drawings, in which:

FIG. 1 is a diagram illustrating one example of a unit electrode according to the present invention;

FIG. 2 is a diagram illustrating a unit element according to the present invention;

FIG. 3 is a diagram illustrating a nanoparticle sensor according to the present invention;

FIG. 4 is a flow diagram illustrating a detection method using the nanoparticle sensor;

FIG. 5 is a photography view of a scanning electron microscope in the nanoparticle sensor which is practically produced according to the present invention.

DETAILED DESCRIPTION OF MAIN ELEMENTS

110: unit electrode
101, 102: electrode pair composing unit electrode
120, 130, 140: metal line

BEST MODE

Hereinafter, the embodiments of the present invention will be described in detail with reference to accompanying drawings. The accompanying drawings are provided as an example sufficiently to deliver an idea of the present invention to the person skilled in the art. Therefore, the present invention is not bounded by the drawings presented hereinafter but can be specified in another form. Further, like reference numerals denote like element throughout the following detailed description of the invention.

At this time, if the technological terms and science terms used herein do not have any other definition, they have meanings that can be typically understood by the person skilled in the art. Further, explanations on known functions and structures which can unnecessary make obscure the subject matter of the present invention in the following description and accompanying drawings will be omitted.

FIG. 1 shows a unit electrode according to the present invention, and the unit electrode 110 is formed to have a nano-gap of a uniform size formed by separating a pair of electrodes 101 and 102 oppositely from each other at a uniform distance L on a substrate S. If a fluid containing the nanoparticles is flowed into the unit electrode 110 in FIG. 1(a) and then the nanoparticles are captured into the nano-gaps as shown in FIG. 1(b), a resistance between the unit electrodes 110 is dramatically reduced in a case of the nanoparticles which are conductive, and an impedance of the nano-gap in the unit electrode 110 is changed in a case of the nanoparticles which are conductive or nonconductive.

As described above, the unit electrode 110 causes electrical changes such as the resistance change and the impedance change by capturing the nanoparticles and becomes a basic element composing the nanoparticle sensor according to the present invention.

The nanoparticle sensor is configured with the unit electrodes to make possible detection of the existence/nonexistence of the nanoparticles and the size of the nanoparticles, and preferably configured with two or more unit electrodes 110 which are operated independently from each other to make possible detection of the concentration of the nanoparticles, the size of the nanoparticles and the size distribution of the nanoparticles based on the number of the unit electrodes 110 which are electrically changed due to the nanoparticles.

Further, the component of the nanoparticles can be identified by treating the substrate residing in the nano-gap formed in the unit electrode 110 with a chemical material which combines or prevents combination with the particular nanoparticle. That is, only the particular nanoparticle can be selectively detected using unimolecular film, biomimetic molecular or various high molecular films which specifically combines with the particular nanoparticle as shown in FIG. 1(c) and FIG. 1(d).

For this purpose, the nanoparticle sensor according to the present invention includes a unit element configured with a plurality of unit electrodes which can apply the voltage independently from each other to one pair of electrodes composing the unit electrode to detect an electrical property.

FIG. 2 shows an example of the unit element 100, which allows 12 unit electrodes 110(1)~110(12) to detect the resistance or the impedance of the unit electrode independently. At this time, it is preferable that one electrode selected from all unit electrodes 110(1)~110(12) composing the unit element 100 is connected to a single metal line 120 and the other electrodes which are not connected to the single metal line 120 are connected to independent metal lines 130, 140 for applying a voltage in the unit electrode in order to cause each unit electrode to detect the resistance or the impedance independently.

Though the unit element 110 is configured with 12 unit electrodes in one example of FIG. 2, it can be configured with more unit electrodes. The more the number of the unit electrodes composing the unit element 100, the reliability and the regeneration of the result is further improved and the measurement error is reduced.

The nanoparticle sensor can be configured with the single unit elements 100 as shown in FIG. 2 and two or more unit elements 100-a, 100-b, 100-c as shown in FIG. 3.

The size of the nanoparticle is detected and analyzed by controlling the size of the nano-gap, particularly a distance L by which the one pair of electrodes is separated, and the size distribution of the nanoparticle can be detected and analyzed by causing the unit electrodes composing the nanoparticle sensor to have the nano-gap size different from each other.

Though FIG. 2 shows the case in which the nano-gap size of all unit electrodes composing the unit element 100 is the same, the unit element 100 can be configured with unit electrodes having the nano-gap size different from one another to detect the size distribution of the nanoparticles.

When detecting the size distribution with one unit element 100, it is preferable that the number of unit electrodes having the same nano-gap size is two or more.

In order to improve reliability and accuracy of the detection, the nanoparticle sensor is preferably configured with a plurality of unit electrodes having the nano-gap of the same size L1, L2 or L3 and also with a plurality of unit electrodes having the nano-gap of the size L1, L2 and L3 different from one another, as shown in FIG. 3. Therefore, the particular unit element can detect only nanoparticle of particular size, and the nanoparticle sensor can be provided with a plurality of unit elements detecting the nanoparticles of size different from one another, whereby it is possible to detect the size distribution of the nanoparticles.

When computing the size distribution of the nanoparticles configured with a plurality of unit elements having the nano-gap of a size different from one another, the sizes L1, L2 and L3 of the nano-gaps correspond to the sizes of the nanoparticles. At this time, a fraction of the size of the nanoparticle may be characterized by dividing the number of the unit electrodes of which the resistance or the impedance is changed of the particular unit element into the number of the unit electrodes of which the resistance or the impedance is changed of all the unit electrodes.

At this time, if the number of the unit electrodes composing each of the plurality of unit elements 100-a, 100b, 100-c is different for each of the unit elements, it is preferable that the number of unit electrodes of which the resistance or the impedance is changed in the same unit element is normalized by total number of unit electrodes composing the unit element, and the number of the unit electrodes of which the resistance or the impedance is changed of all the unit elements is normalized by total number of unit electrodes composing the nanoparticle sensor.

If the nanoparticle sensor is configured with a single unit element as shown in FIG. 2 or the nanoparticle sensor is configured with a plurality of unit elements as shown in FIG. 3, the concentration of the nanoparticles is computed based on a value computed by dividing the total number of the unit electrodes of which the resistance or the impedance is changed into the total number of the unit electrodes composing the nanoparticle sensor.

As described above, the nanoparticles can be detected by causing a function group of a unimolecular film, a bio mimetic molecular or a various high molecular films uniquely combining with a particular nanoparticle to be formed on a surface of the nano-gap.

Similarly to FIG. 2 and FIG. 3, only particular nanoparticle may be selectively detected by composing the unit element with a plurality of unit electrodes having the nano-gap in which the function group different from each other.

Further, it is preferable that the unit element has the nano-gap in which the same function group is formed to improve accuracy, sensitivity and regeneration in the measurement, and the nanoparticle sensor is configured with a plurality of unit elements having different function group from each other. At this time, it is possible to analyze the size, the concentration and the size distribution of the particular nanoparticle using a method similar to that described above referring to FIG. 2 and FIG. 3.

Subsequently, it is possible to detect the kind, the concentration, the size and the size distribution of the nanoparticles by measuring the resistance or the impedance of each unit element composing the nanoparticle sensor to measure the number of the unit electrodes of which the resistance or the impedance is changed.

For the purpose of it, after measuring a reference value by measuring the resistance or the impedance of each of the unit electrodes composing the nanoparticle sensor as shown in FIG. 4, the fluid containing the nanoparticles is induced into the nanoparticle sensor according to the present invention. The fluid containing the nanoparticles can be a gas (air) into which the nanoparticles are dispersed or a liquid into which the nanoparticles are dispersed. At this time, a pressure or vibration can be applied to the fluid.

After passing a certain time, it detects the number of the unit electrodes of which the resistance or the impedance is changed, by re-measuring the resistance or the impedance of each of unit electrodes composing the nanoparticle sensor and comparing the reference value with the re-measured value.

After inducing the nanoparticles, the existence/nonexistence of the nanoparticle, the size of the nanoparticle, the concentration of the nanoparticle, the size distribution of the nanoparticle and the component of the nanoparticle can be identified by the number of the unit electrodes having changed resistance or impedance. At this time, the re-measurement is performed after removing the fluid induced and making measuring conditions similar to the measuring conditions of the reference value, and the step of rinsing the nanoparticle sensor with the fluid which is not containing the nanoparticles is performed in order to remove the nanoparticles which are non-uniquely absorbed into the nanoparticle sensor after the fluid is removed.

In order to reduce the measurement error, it is preferably determined that the nanoparticles are absorbed into the nano-gap formed in the unit electrode if the changed value of the resistance or the impedance is greater than threshold value by comparing the reference value with the re-measurement value for each of the unit electrodes. The threshold value is determined by the size of the nanoparticles, physical parameters of materials and the object to be measured, and physical parameters of the nanoparticle sensor configured with the unit electrode.

Only unit electrode having a change value in the resistance, the electric capacitance, or the impedance greater than the threshold value can be considered to be a unit electrode which is electrically changed by the nanoparticles, in which the change value in the resistance or impedance of the unit electrode can be converted into the number of the nanoparticle captured into the nano-gap of the unit electrode so that the existence/nonexistence, the size, the concentration, the size distribution, and the component of the nanoparticle can be analyzed.

This is because the resistance or the impedance is changed by the nanoparticles captured into unitary nano-gap formed in the unit electrode, and particularly the unit electrode is preferably configured with electrode of large-area. The number of nanoparticles captured into the nano-gap for the resistance or the impedance (or changed value of resistance or electric capacity) of unit electrode is tabled for each size of the nano-gap and used for the conversion.

At this time, the concentration or the size distribution of the nanoparticles can be analyzed by replacing the number of the unit electrodes electrically changed by the nanoparticles with the number of the nanoparticles converted.

The nanoparticle sensor according to the present invention further includes row/column decoders which enable easily performing electrical measurement on the plurality of unit electrodes composing the unit element, further includes a memory which can store the reference value and the re-measurement value of each unit electrode, the threshold value, measurement condition (waveform of voltage applied to the unit electrode, applying time and the like), the nano-gap size of each unit electrode, a kind of function group formed on each unit electrode, and further includes a typical digital signal processor (DSP) which is inputted with measurement results of each unit electrode detected according to the measurement conditions to analyze the size, the size distribution, the concentration, and the component of the nanoparticles.

Since the substrate having the unit element formed thereon provides physical support, the function group combining with the nanoparticle can be held on the substrate.

The substrate may be used with anything if it has an electric insulating property, in which the electric insulating material is preferably used with oxide system, and more preferably used with silicon oxide.

The unit electrode which is a basic element composing the unit element can be patterning via a typical method selected from the lithographic method, printing method and contact print method or produced based on a method of manufacturing the nano-gap electrode of a Korean Application No. 2006-0039528 filed by the present inventors so that a separated distance between one pair of electrodes composing the unit electrode can be controlled in a range of 1 nm to 1 µm.

FIG. 5 is a photograph view of a Scanning Electron Microscopy in the nanoparticle sensor according to the present invention manufactured as a unit element having 40 unit electrodes.

First, it prepares forty unit electrodes having the nano-gap size different from one another by controlling the separated distance between individual unit electrodes to allow the separated distance between one pair of electrodes composing the unit electrode to be 100 nm to 1 µm, using photo lithography and E-beam lithography method on the silicon substrate having the oxide film formed thereon, and then forms unimolecular film having —HN2 function group uniquely combining with gold nanoparticle on a surface of the substrate having the nano-gap formed thereon using aminopropyltriethoxysilane after activating the surface of the substrate by $O_2$ plasma treatment.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

INDUSTRIAL APPLICABILITY

The nanoparticle sensor can be utilized from development of nano-material detecting technology, to variable fields of such as nano stability, nanoparticle-related industry site, environment supervisor system and sensor Kit development.

Further, the nanoparticle sensor according to the present invention can be combined with a technology for processing conforming to medium to be measured such as a gas or a liquid, a technology for controlling reaction of the nanoparticle with functional surface, a peripheral technology for manufacturing the detector to implement the best performance, whereby it is possible to provide the nanoparticle sensor which is feasible in production on a large scale and convenient to be used.

The invention claimed is:

1. A nanoparticle sensor for detecting nanoparticles, the nanoparticle sensor comprising:
   a unit element configured with a plurality of unit electrodes which are electrically operated independently from each other;
   a row/column decoder performing electrical measurement on the plurality of unit electrodes; and
   a digital signal processor analyzing a size, a size distribution and a concentration of the nanoparticles,
   wherein each of the unit electrodes comprises one pair of electrodes separated at a distance to have a nano-gap, and the nanoparticles are detected by measuring an electric change caused due to the nanoparticles captured into the nano-gap, and
   wherein a size of the nano-gap corresponds to a size of the nanoparticle.

2. The nanoparticle sensor according to claim 1, wherein the concentration of nanoparticles is analyzed from the number of the unit electrodes which are electrically changed due to the nanoparticles captured into the nano-gaps.

3. The nanoparticle sensor according to claim 1, wherein the nanoparticle sensor analyzes the size of the nanoparticles by controlling the size of the nano-gap.

4. The nanoparticle sensor according to claim 3, wherein the unit element is configured with the plurality of unit electrodes having the size of the nano-gap different from one another.

5. The nanoparticle sensor according to claim 3, wherein the unit element has the nano-gaps of the same size, and the nanoparticle sensor is configured with a plurality of unit elements having the size of the nano-gaps different from one another.

6. The nanoparticle sensor according to claim 5, wherein the size distribution of the nanoparticles is characterized by the number of the unit electrodes of which a resistance or an impedance is changed of the same unit element for each of the plurality of unit elements.

7. The nanoparticle sensor according to claim 1, wherein a function group combining with a nanoparticle is formed on a surface of the nano-gap.

8. The nanoparticle sensor according to claim 7, wherein the unit element is configured with the plurality of unit electrodes having the nano-gaps in which a function group different from one another is formed.

9. The nanoparticle sensor according to claim 7, wherein the unit element has the nano-gaps in which the same function group is formed, and the nanoparticle sensor is configured with the plurality of unit elements in which the function group different from one another is formed.

10. The nanoparticle sensor is according to claim 1, wherein the electric change comprises a change in a resistance or an impedance of the unit electrode.

11. The nanoparticle sensor according to claim 2, wherein the concentration of the nanoparticles is characterized by dividing a total number of the unit electrodes of which a resistance or an impedance is changed into a total number of the unit electrodes composing the unit element.

12. The nanoparticle sensor according to claim 2, wherein one electrode selected respectively from all the unit electrodes composing the unit element is connected to a single metal line.

13. The nanoparticle sensor according to claim 12, wherein the other electrodes not connected to the single metal line of the unit electrodes are connected to an independent metal line for applying a voltage, respectively.

* * * * *